(12) United States Patent
Niwa et al.

(10) Patent No.: US 7,700,352 B2
(45) Date of Patent: Apr. 20, 2010

(54) COMPOSITION FOR CULTURING MOUSE PLURIPOTENT STEM CELLS

(75) Inventors: Hitoshi Niwa, Nara (JP); Kazuya Ogawa, Kobe (JP)

(73) Assignee: Riken, Saitama (JP)

( * ) Notice: Subject to any disclaimer, the term of this patent is extended or adjusted under 35 U.S.C. 154(b) by 999 days.

(21) Appl. No.: 10/532,579

(22) PCT Filed: Oct. 31, 2003

(86) PCT No.: PCT/JP03/14009

§ 371 (c)(1),
(2), (4) Date: Dec. 6, 2005

(87) PCT Pub. No.: WO2004/039965

PCT Pub. Date: May 13, 2004

(65) Prior Publication Data

US 2006/0127370 A1    Jun. 15, 2006

(30) Foreign Application Priority Data

Oct. 31, 2002  (JP) .............................. 2002-318052

(51) Int. Cl.
*C12N 5/00* (2006.01)
*C12N 5/02* (2006.01)
*C12N 5/04* (2006.01)

(52) U.S. Cl. .................. 435/375; 435/377; 435/383; 435/384; 435/387; 435/392

(58) Field of Classification Search .................. None
See application file for complete search history.

(56) References Cited

U.S. PATENT DOCUMENTS

| 4,415,546 | A | 11/1983 | Ramachandran et al. |
| 6,132,957 | A | 10/2000 | Johnson et al. |

FOREIGN PATENT DOCUMENTS

| CN | 1219134 A | 6/1999 |
| EP | 0911034 | 4/1999 |
| WO | WO-90/01541 A | 2/1990 |
| WO | WO-97/20035 A1 | 6/1997 |
| WO | WO-02/00847 A2 | 1/2002 |
| WO | WO-02/04475 | 1/2002 |

OTHER PUBLICATIONS

Gracia-Navarro et al. Pituitary Adenylate Cyclase-Activating Polypeptide Stimulates Calcium Mobilization in Amphibian Pituitary Cells. Endocrinology. 1992, vol. 131, pp. 1069-1074.*

Schorr et al. Multiple Specific Hormone Receptors in the Adenylate Cyclase of an Adrenocortical Carcinoma. Journal of Biolog. Chem. 1971, vol. 246, pp. 5806-5811.*

Yasuda et al. Interaction Between Brain Natriuretic Peptide and Atrial Natriuretic Peptide in Caecal Smooth Muscle Cells. Regulatory Peptides. 2000, vol. 86, pp. 125-132.*

Pera et al. Human Embryonic Stem Cells. Journal of Cell Sci. 2000, vol. 113, pp. 5-10.*

Shamblott et al. Derivation of Pluripotent Stem Cells from Cultured Human Primoridal Germ Cells. Proced. Natl. Acad. Sci. (USA). 1998, vol. 95, pp. 13726-13731.*

Wenyu et al., Chinese Journal of Histochemistry and Cytochemistry, vol. 10, No. 3, Sep. 2001, p. 1 with English language abstract only.

Pesce et al., Development, 1996, vol. 122, No. 1, pp. 215-221.

De Felici et al., Int. J. Dev. Biol., 2000, vol. 44, pp. 575-580.

Lipskaia et al., J. Cell. Physiol., 1998, vol. 176, No. 1, pp. 50-56.

Deng et al., Biochem Biophys. Res. Comm., 2001, vol. 282, No. 1, pp. 148 to 152.

Chen et al., Lab. Invest., 1998, vol. 78, No. 2, pp. 165-174.

Marchal et al., Exp. Cell. Res., 1995, vol. 220, No. 1, pp. 1-10.

Lelievre et al., "Fibroblast Growth Factor-2 Converts PACAP Growth Action on Embryonic Hindbrain Precursors From Stimulation to Inhibition," Journal of Neuroscience Research vol. 67, No. 5, pp. 566-573 (Mar. 1, 2002).

Hirose et al., "Gene Expression of PACAP and Its Receptors in the ES Cell-Derived Neuronal Stem Cells," Japanese Journal of Pharmacology, the Japanese Pharmacological Society, vol. 88, Suppl. 1, p. 143P (Mar. 13, 2002).

Ogawa et al., "A Novel Mechanism for Regulating Clonal Propagation of Mouse ES Cells," Genes to Cells, vol. 9, No. 5, pp. 471-477 (May 2004).

White, Richard E. et al., The Activation of BK_(Ca) Channel in Porcine Coronary Vascular Smooth Muscle Cells Induced by Dopamine and its Signal Transduction, Chinese Journal of Applied Physiology, vol. 16, No. 1, pp. 1 (2000), with English language Translation.

Patel, Tarun B., et al., Molecular biological approaches to unravel adenylyl cyclase signaling and function, Gene, vol. 269, pp. 13-25, (2002).

State Intellectual Property Office of People's Republic of China, "The Third Office Action," Appl. No. 200380102403.7, Issued Dec. 12, 2008.

Master Dissertation of the Second Military Medical University, "Study of the Effect and Mechanism of Placental Corticotropin-Releasing Hormone in Human Parturition," May 2001, Abstract.

* cited by examiner

*Primary Examiner*—Deborah Crouch
(74) *Attorney, Agent, or Firm*—Birch, Stewart, Kolasch & Birch, LLP

(57) ABSTRACT

The invention aims to proliferate or establish undifferentiated pluripotent stem cells that retain their differentiation potency by culturing pluripotent stem cells in a medium free of a feeder cell, or a serum. The aim is attained by using a culture medium for pluripotent stem cells comprising the known ingredients, which is supplemented with an inhibitor of an adenylate cyclase activity.

15 Claims, 1 Drawing Sheet

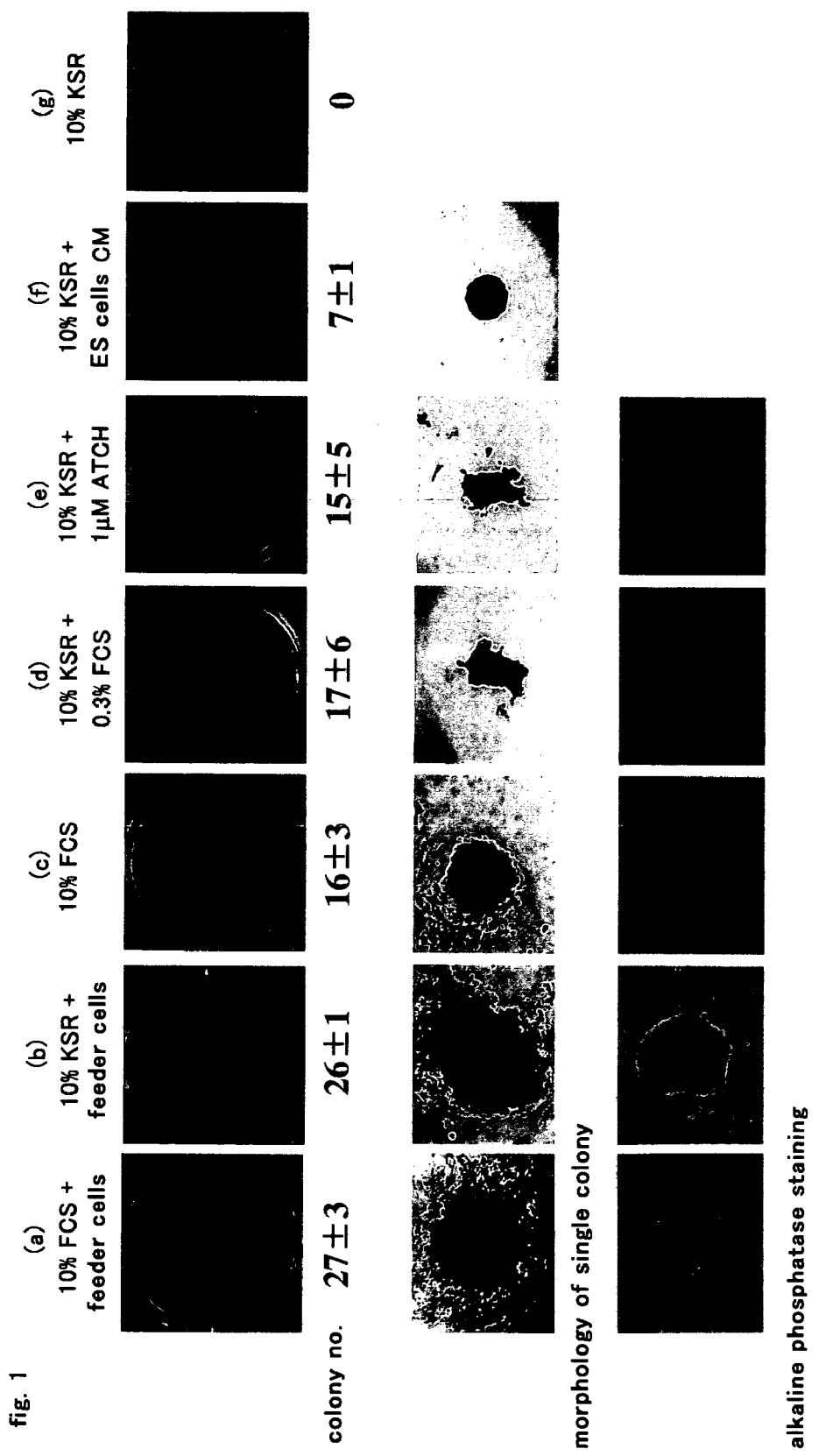

US 7,700,352 B2

COMPOSITION FOR CULTURING MOUSE PLURIPOTENT STEM CELLS

The present application is a National Stage entry of PCT/JP2003/014009 filed on Oct. 31, 2003. Priority is also claimed to Japanese patent application 2002-318052 filed Oct. 31, 2002 under 35 U.S.C. §119.

FIELD OF THE INVENTION

This invention relates to a composition for the culture of pluripotent stem cells and use thereof, and specifically to a composition that makes it possible to culture pluripotent stem cells in a medium free of a feeder cell or a serum, a medium comprising the same, and use thereof.

BACKGROUND ART

Pluripotent stem cells are self-replicating stem cells that have an ability to differentiate into differentiated cell types, each of which belongs to at least one of ectoderm, mesoderm, and endoderm, and the cells include embryonic stem cells (ES cells), embryonic germ cells (EG cells), embryonal carcinoma cells (EC cells), multipotent adult progenitor cells (MAP cells), and adult pluripotent stem cells (APS cells). Among them, ES cells are illustrated as shown below to describe the invention of the present application.

ES cells are a cell population that is derived from pluripotent stem cell clones comprised in an early embryo, and have an ability to differentiate into diverse cell types including germ cells. ES cells can be proliferated while retaining their pluripotency in a defined culture condition. When ES cells thus cultured in such a culture condition are injected into a blastocyst or a morula, chimeric animals having two different genomes are produced. Chimeric animals that have germ cells derived from the ES cells genetically manipulated may be bred with each other to create animal individuals with a manipulated gene. Thus, ES cells are widely utilized to produce transgenic animals including knockout mice wherein the function of a certain gene is altered. On the other hand, the technical approach to induce the differentiation of ES cells in a dish to provide a certain differentiated cells has been developed. Since the approach is applied to human ES cells to provide differentiated cells necessary in cell transplantation therapy, it is expected that ES cells would be used in the medical field in future.

As described above, the approach to proliferate or establish ES cells while retaining their pluripotency (differentiation potency) without differentiating has been developed, in which the culture medium used for the culture of ES cells usually comprises a serum, including specifically a fetal calf serum (FCS), a horse serum, or goat serum. Serums suppress the differentiation of ES cells, and supply various liquid factors to promote the proliferation or establishment of the ES cells. However, the identities of the liquid factors have not been known yet, and the serum varies in quality depending on production lot. Accordingly, it would be required to select an appropriate serum lot by a preparative screening, which demands a large amount of labor.

As another culture approach, ES cells are seeded and cultured in a medium that comprises, as feeder cells, primary cultures of embryonic fibroblasts inactivated to inhibit the proliferation or STO cells. In this approach, the feeder cells are understood to form a matrix for ES cell attachment, as well as to suppress the ES cell differentiation, and to release various liquid factors that promote the ES cell proliferation. Since leukemia inhibitory factor (LIF), which has been known as one of such liquid factors (U.S. Pat. No. 5,187,077) has a potency to suppress the differentiation of ES cells derived from various animals, a combination with a serum, a feeder cell, and LIF are frequently used. Further, it has been suggested that a large amount of the recombinant LIF protein could be added to a serum-containing medium to culture ES cells in a feeder cell-independent manner on a gelatin-coated plate (U.S. Pat. No. 5,166,065).

Use of a serum or a feeder cell as shown above causes major problems for the application of differentiated cells derived from human ES cells to cell transplantation therapy. Specifically, human ES cells have been usually cultured in a medium containing a fetal calf serum using primary cultures of mouse embryonic fibroblasts as feeder cells, and such heterologous biological components as used therein may be necessarily the source of unknown pathogen contamination. Further, transplantation of human cells co-cultured with heterologous cells should be regarded as xenotransplantation, and recipients undergoing such transplantation are forced to live in restricted circumstances according to the draft guideline of the U.S. Food and Drug Administration.

Under the circumstances, it is apparently desirable that pluripotent stem cells such as ES cells to be used in analysis in cell biology and in medical applications should be isolated and cultured using a medium free of pathogen from a heterologous animal and of heterologous cells, specifically a medium which is free of a feeder cell and a serum, which can be artificially prepared, and which comprises the known ingredients.

In response to the demand, many studies have been conducted and proposed. Representative study includes a culture technique wherein a large amount of the recombinant LIF protein is added to a serum-containing medium to culture ES cells in a feeder cell-independent manner on a gelatin-coated plate (U.S. Pat. No. 5,166,065). Further, a culture medium for embryonic stem cells comprising a defined replacement in stead of a serum has been proposed (Japanese Patent Publication (kokai) No. 2001-508302), which allows to culture the cells in the presence of feeder cells in a medium free of serum. However, even if the medium comprising known ingredients which comprises a defined replacement in stead of a serum, is supplemented with a large amount of the recombinant LIF protein, it has been impossible to stably culture ES cells in a feeder cell-independent manner on a gelatin-coated plate. In other words, when cultured using a serum replacement in stead of a serum according to the conventional manner, the feeder cell-independent ES cells have not been capable of being proliferated or established on a gelatin-coated plate under a condition that the cells are seeded at a lower density.

There is a demand to proliferate ES cells even under a condition that the cells are seeded at a lower density in the establishment and the genetic engineering of ES cells, but the demand cannot be satisfied by the approaches as shown above.

DISCLOSURE OF THE INVENTION

The technical problem according to the invention of the present application is to provide a process for the culture of pluripotent stem cells in a medium which can be artificially prepared, and which comprises the known ingredients without feeder cell and serum, which process for the culture has not been previously believed impossible.

The present inventors conducted enormous research for solving the problem as mentioned above, and, as a result, found the solution of the problem that pluripotent stem cells could be cultured under a condition that an adenylate cyclase activity is inhibited to proliferate or establish the pluripotent stem cells while maintaining the cells in an undifferentiated state, thereby accomplishing the present invention.

Typical embodiment for fulfilling "a condition that an adenylate cyclase activity is inhibited" is to add an inhibitor of an adenylate cyclase activity to a culture medium of pluripotent stem cells, or to combine the inhibitor with the culture medium. This makes it possible to proliferate or establish the pluripotent stem cells that retain their differentiation potency without differentiating, even in the absence of feeder cells or serum in the culture medium.

As such, the present invention in a main aspect provides a composition for the culture of pluripotent stem cells, which comprises at least one inhibitor of an adenylate cyclase activity. In another aspect, the invention provides a medium for the culture of pluripotent stem cells, which comprises said composition. In the further aspect, the invention provides a process for the culture of pluripotent stem cells which comprises using said medium. In the still further aspect, the invention provides an undifferentiated pluripotent stem cell proliferated or established, which is cultured in said medium. Those and other aspects will be apparent from the detailed description hereinafter for those skilled in the art.

In an aspect, the invention provides a composition for the culture of pluripotent stem cells, which comprises at least one inhibitor of an adenylate cyclase activity. The composition of the invention may be a medium supplement. The composition of the invention is to proliferate pluripotent stem cells while maintaining the cells in an undifferentiated state. Preferably, the inhibitor of an adenylate cyclase activity is selected from the group consisting of SQ22536 (9-(tetrahydro-2-furanyl)adenine), 2',5'-dideoxyadenosine, 9-cyclopentyladenine, 2',5'-dideoxyadenosine 3'-diphosphate, 2',5'-dideoxyadenosine 3'-monophosphate, and MDL-12,330A (cis-N-(2-phenylcyclopentyl)azacyclotridec-1-en-2-amine), or is selected from the group consisting of adrenocorticotropic hormone (ACTH), brain natriuretic peptide (BNP), pituitary adenylate cyclase activating polypeptide (PACAP), and a peptide having a physiological activity substantially similar to them.

In another aspect, the invention provides a medium for the culture of pluripotent stem cells, which comprises any one of the compositions as described above. Preferably, the medium is free of a feeder cell, and/or a serum. More preferably, the medium is free of both feeder cell and serum. The medium may be a minimum medium for cell culture, and may comprise further a differentiation inhibitory factor, a serum replacement and an antioxidant.

In a further aspect, the invention provides a process for the culture of pluripotent stem cells, which comprises culturing the pluripotent stem cells under a condition that an adenylate cyclase activity is inhibited, said process allowing to proliferate or establish the pluripotent stem cells while maintaining the cells in an undifferentiated state. Preferably, the condition that an adenylate cyclase activity is inhibited involves the use of an inhibitor of an adenylate cyclase activity. The culture process may be performed using the medium as described above.

In the culture process according to the invention, the pluripotent stem cells are preferably ES cells. The pluripotent stem cells may be derived from a mammal. The pluripotent stem cells may be derived from a human.

The invention also provides an undifferentiated pluripotent stem cell, which is proliferated or established according to the process as described above.

In the still further aspect, the invention provides a process for the preparation of a clonal population of undifferentiated pluripotent stem cells, which comprises culturing the undifferentiated pluripotent stem cells under a condition that an adenylate cyclase activity is inhibited. Further, the invention provides a process for the preparation of a clonal population of undifferentiated pluripotent stem cells, which comprises isolating undifferentiated pluripotent stem cells from a living body, and culturing the undifferentiated pluripotent stem cells under a condition that an adenylate cyclase activity is inhibited. Preferably, the condition that an adenylate cyclase activity is inhibited involves the use of an inhibitor of an adenylate cyclase activity. The culture step of the process may be performed using the medium as described above.

Preferably, the process for the preparation is characterized in that one pluripotent stem cell is cultured to provide a clonal population of the cells. Alternatively, the process for the preparation is characterized in that pluripotent stem cells are cultured in the medium as described above to provide a clonal population of the cells, in which the pluripotent stem cells are seeded at a lower density than that which allows adjacent pluripotent stem cells to interact with each other so as to induce the proliferative, undifferentiated pluripotent stem cells, or in that pluripotent stem cells are cultured in the medium as described above to provide a clonal population of the cells, in which the pluripotent stem cells are not proliferated while maintaining an undifferentiated state under the condition that neither feeder cells and/or serums, nor the medium as described above is used. Most preferably, the process for the preparation is characterized in that one pluripotent stem cell is cultured in the medium as described above to provide a clonal population of the cells.

In the process for the preparation as described above, the pluripotent stem cells are preferably ES cells. The pluripotent stem cells may be derived from a mammal. The pluripotent stem cells may be derived from a human.

The invention also provides clonal population of undifferentiated pluripotent stem cell, which is obtainable by the process for the preparation as described above.

In the still further aspect, the invention provides a use of an inhibitor of an adenylate cyclase activity or a composition comprising an inhibitor of an adenylate cyclase activity, for culturing pluripotent stem cells while maintaining the cells in an undifferentiated state to proliferate or establish the undifferentiated cells.

The present inventions make it possible to proliferate or establish undifferentiated pluripotent stem cells that retain their multi-differentiation potency in a medium comprising the known ingredients free of feeder cells and serums. The pluripotent stem cells proliferated or established thus obtained are free of contamination with pathogen from serums or feeder cells, and avoid the restricted circumstances due to the co-culture with heterologous cells.

BRIEF DESCRIPTION OF DRAWINGS

FIG. 1 depicts a photograph showing the proliferations of undifferentiated ES cells by means of supplementing with indicated peptides in the absence of serums and feeder cells.

BEST MODE FOR CARRYING OUT THE INVENTION

As used herein, the term "pluripotency" refers to an ability to differentiate into differentiated cell types which belong to all of ectoderm, mesoderm and endoderm, and an ability to differentiate into differentiated cell types, each of which belongs to at least one of ectoderm, mesoderm and endoderm. An ability to differentiate into germ cells is also included in the term.

The term "pluripotent stem cells" refers to self-replicating stem cells that have an ability to differentiate into differentiated cell types, each of which belongs to at least one of ectoderm, mesoderm, and endoderm (multi-differentiation potency), and the stem cells include ES cells, EG cells, EC cells, MAP cells, and APS cells. Representative stem cells, embryonic stem cells (ES cells), have a multi-differentiation potency, and can differentiate into diverse cells including germ cells, when injected into another blastocyst.

The term "feeder cells" refers to cells that have a metabolic activity without self-propagating, and that produce various metabolites to assist the proliferations of other cells seeded on the feeder cells (See Masami Muramatsu et al., "Bunshisai-boseibutsugaku Jiten" p367, 1997, TOKYO KAGAKU DOZIN, CO., LTD.). For example, primary cultures of embryonic fibroblasts that are inactivated to inhibit the proliferation or STO cells are used as feeder cells in case of ES cells.

The term "feeder cell-independent pluripotent stem cells" refers to pluripotent stem cells that can be proliferated under a culture condition wherein any feeder cell is not involved in the presence of a serum. Normally, pluripotent stem cells are hardly proliferated while maintaining the cells in an undifferentiated state under such condition, but they will proliferate in a feeder cell-independent manner when repeatedly subcultured.

Compositions for the culture of pluripotent stem cells as provided according to the present invention are characterized in that the compositions comprise at least one inhibitor of an adenylate cyclase activity. Adenylate cyclase is an enzyme which converts ATP to cAMP (cyclic AMP), and plays a central role in cellular signal transduction. The activity of the enzyme is regulated mainly via G-protein-coupled receptors by various extracellular signals, and the cAMP produced functions as an intracellular second messenger. A total of 10 adenylate cyclases have been reported to exist in mammals such as human, mouse, rat, bovine, dog, and rabbit (for example, Patel, TB et al., Molecular biological approaches to unravel adenylyl cyclase signaling and function, Gene, 269, 13-25, 2001). The genes of the nine enzymes among them were isolated in human, whereas the genes of the five were isolated in mice. The sequences of the isolated genes are conserved between mice and human, and those molecules are essential in basal vital phenomenon including cell proliferation control, thus believing that the functions of adenylate cyclases in pluripotent stem cells are also conserved in these mammals.

Inhibitors of an adenylate cyclase activity as used in the compositions for the culture of pluripotent stem cells according to the present invention may function at each stage of extracellular and intracellular signal transduction systems so long as they result in the inhibition of adenylate cyclase activities. For example, useful inhibitors include agents that transmit an extracellular signal leading to the inhibition of an adenylate cyclase activity to a receptor, and agents that directly inhibit an adenylate cyclase activity, and agents that function on a molecule that mediates a signal transduction between a receptor and an adenylate cyclase may be also used.

In order to examine whether or not a substance inhibits the adenylate cyclase activity of pluripotent stem cells, the substance is added to a culture medium of cells (for example ES cells) to be proliferated or established, and an inhibitory level of cAMP production is checked.

Examples of agents that directly inhibit an adenylate cyclase activity include SQ22536 (9-(tetrahydro-2-furanyl) adenine), 2',5'-dideoxyadenosine, 9-cyclopentyladenine, 2',5'-dideoxyadenosine 3'-diphosphate, 2',5'-dideoxyadenosine 3'-monophosphate, MDL-12,330A (cis-N-(2-phenylcyclopentyl)azacyclotridec-1-en-2-amine), and a similar compound, all of which are readily available since they are offered commercially by CALBIOCHEM-NOVABIOCHEM CORPORATION (California, USA) or the like. Amount of those compounds may be determined appropriately depending on what kind of a compound is used. In case of SQ22536, for example, the final concentration in a medium are not specifically limited, and usually SQ22536 may be used in a final concentration from 1 µM to 10 mM, preferably 10 µM to 1 mM.

Other examples of agents that inhibit the adenylate cyclase activity of pluripotent stem cells include adrenocorticotropic hormone (ACTH, corticotropin), brain natriuretic peptide (BNP), pituitary adenylate cyclase activating polypeptide (PACAP).

Additionally, a peptide having a physiological activity substantially similar to those peptides may be used, which is a peptide that comprises an amino acid sequence wherein one or more amino acid residues of the amino acid sequence composed of such peptides as ACTH, BNP, and PACAP are deleted, substituted and/or added, and that has a physiological activity substantially similar to the corresponding full-length peptide. For example, as to ACTH that is composed of 39 amino acid residues (ACTH (1-39)), it has been known that the amino acids positioned from the N-terminus 1 to 24 share in various animals, whereas the amino acids positioned from 25 to 33 vary depending on particular animals, and that the amino acids positioned from the N-terminus 1 to 18 exerts adrenocorticotropic actions, and therefore, in addition to ACTH (1-39), its fragments, ACTH (1-24), ACTH (11-24), or the like may be used according to the invention. Those peptides may be usually used in a final concentration from 1 nM to 100 µM, preferably 1 to 10 µM.

All of ACTH, BNP, PACAP, and a fragment thereof are described in literatures such as U.S. Pat. No. 4,415,546, and Kazutomo Imahori, et al. Seikagaku Jiten (3ed.) pp 1178 to 1179, p 721, and pp 286 to 287 (1998), Tokyo Kagaku Dojin, or are commercially available as reagents, or are may be prepared according to the methods described in literatures. For example, those peptides can be prepared according to common methods for a construction of a desired amino acid sequence for those skilled in the art. Alternatively, they may be prepared via genetic engineering procedures wherein by a gene encoding the peptide is inserted into a host cell such as *E. coli*, and then the peptide expressed is isolated and purified.

A composition of the present invention may comprise a single inhibitor of an adenylate cyclase activity, and may comprise any combination of two or more inhibitors of an adenylate cyclase activity. According to the invention, specifically, a composition comprising two or more compounds, a composition comprising two or more peptides, and a composition comprising both a compound and a peptide, may be used, and alternatively, a composition comprising a single inhibitor of an adenylate cyclase activity may be also used.

The invention of the present application provides a medium for the culture of pluripotent stem cells, which is added with a composition described above. The composition may be used as an alternative to liquid factors derived from feeder cells or serums. Although the existence of feeder cells or serums in a culture medium does not bring about any obstacle to the culture of pluripotent stem cells, the culture medium without feeder cells and/or serums is preferably used, and more preferably, the culture medium with neither cells nor serum is used, since existence of feeder cells or serums in a culture medium necessarily accompanies contamination with pathogen therefrom, and the restricted circumstances due to the heterologous cells.

In other words, a preferred culture medium of the present invention is a culture medium comprising a cell culture minimum medium (CCMM) as a minimal essential medium, and further comprising a differentiation inhibitory factor, a serum replacement and an antioxidant such as 2-mercaptoethanol (2-ME), dithiothreitol, ascorbic acid, as well as a composition of the present invention (i.e., an inhibitor of an adenylate cyclase activity), which medium is free of a feeder cell and a serum. All of CCMM, a differentiation inhibitory factor, a serum replacement, an antioxidant, and a composition of the present invention are known substances that can be artificially prepared, and therefore a culture medium composed of those ingredients can avoid unknown pathogen contamination due to the use of components from living bodies.

The term "cell culture minimum medium (CCMM)" used as a minimal essential medium refers to any medium that makes it possible to proliferate pluripotent stem cells while maintaining the cells in an undifferentiated state, when added thereto with a differentiation inhibitory factor, a serum replacement, an antioxidant, and a composition of the present invention.

CCMM usually comprises a common inorganic salt such as zinc, iron, magnesium, calcium, and potassium, a vitamin, glucose, a buffer system, an essential amino acid, and the like. Examples of CCMM include Dulbecco's Modified Eagle's Medium (DMEM), Minimal essential Medium (MEM), Basal Medium Eagle (BME), RPMI1640, F-10, F-12, α Minimal essential Medium (αMEM), Glasgow's Minimal essential Medium (GMEM), Iscove's Modified Dulbecco's Medium, all of which may be commercially available.

Most preferred CCMM is GMEM having the composition described in Table 1.

TABLE 1

| ingredients | concentrations (mg/L) |
| --- | --- |
| CaCl$_2$ (anhydrous) | 200.00 |
| Fe (NO$_3$)$_3$ 9H$_2$O | 0.10 |
| KCl | 400.00 |
| MgSO$_4$ (anhydrous) | 97.67 |
| NaCl | 6400.00 |
| NaHCO$_3$ | 2750.00 |
| NaH$_2$PO$_4$ H$_2$O | 107.80 |
| D-glucose | 4500.00 |
| phenol red | 16.00 |
| L-arginine HCl | 42.00 |
| L-cysteine HCl | 31.29 |
| L-glutamine | 292.00 |
| L-histidine HCl H$_2$O | 21.00 |
| L-isoleucine | 52.40 |
| L-leucine | 52.40 |
| L-lysine HCl | 73.10 |
| L-methionine | 15.00 |
| L-phenylalanine | 33.00 |
| L-threonine | 47.60 |
| L-tryptophan | 8.00 |
| L-tyrosine 2Na 2H$_2$O | 52.19 |
| L-valine | 46.80 |
| D-Calcium pantothenic acid | 2.00 |
| choline chloride | 2.00 |
| folic acid | 2.00 |
| i-inositol | 3.60 |
| niacinamide | 2.00 |
| pyridoxal HCl | 2.00 |
| riboflavin | 0.20 |
| thiamin HCl | 2.00 |

Preferably, CCMM comprises 0.1 mM non-essential amino acid, and 1 mM sodium pyruvate. Non-essential amino acid as used herein includes a mixture of L-alanine, L-aspar-agine, L-asparatic acid, L-glutamic acid, glycine, L-proline, and L-serine, which is commercially available as MEM non-essential amino acids solution 10 mM liquid (Invitrogen). Sodium pyruvate as used herein includes MEM Sodium pyruvate solution 100 mM liquid (Invitrogen), which is commercially available.

A differentiation inhibitory factor is a liquid factor released by a feeder cell and a pluripotent stem cell, and inhibits the differentiation of an undifferentiated cell. Representative differentiation inhibitory factor include leukemia inhibitory factor (LIF). It is preferred that differentiation inhibitory factors are artificially prepared from economic viewpoint, and in view of avoidance of pathogen contamination which would involve the isolation of the factors from living bodies, which isolation is possible since the factors are inherently biological substances. In case of a proteinous differentiation inhibitory factor such as LIF, a recombinant protein of the differentiation inhibitory factor that is prepared via genetic engineering is preferably used.

2-Mercaptoethanol, dithiothreitol, ascorbic acid, or the like may be used as an antioxidant, and usually 2-mercaptoethanol is used. Those compounds are offered commercially, and readily available.

A serum replacement is a substance that supports the proliferation of pluripotent stem cells when added to a serum-free culture medium. A serum replacement may be a single substance or a mixture of the substances, and specifically comprises one or more ingredients that is selected from the group consisting of an albumin such as bovine serum albumin; or an albumin replacement such as bovine pituitary extracts, rice hydrolysates, fetal calf albumin, ovalbumin, human serum albumin, bovine embryo extracts, and AlbuMAX I (Registered Trademark); an amino acid such as glycine, L-alanine, L-asparagine, L-cysteine, L-asparatic acid, L-glutamic acid, L-phenylalanine, L-histidine, L-isoleucine, L-lysine, L-leucine, L-glutamine, L-arginine, L-methionine, L-proline, L-hydroxyproline, L-serine, L-threonine, L-tryptophan, L-tyrosine, and L-valine; a vitamin; transferrin or a transferrin replacement such as an iron-chelating agent including ethylene diamine tetra-acetic acid, ethylene glycol-bis(β-aminoethyl ether)-N,N,N',N'-tetra-acetic acid, deferoxamine mesylate, dimercaptopropanol, diethylenetriamine pentaacetic acid, and trans-1,2-diaminocyclohexan-N,N,N',N'-tetra-acetic acid, and an iron-chelated compound including ferric citrate chelate and ferrous sulfate chelate; an antioxidant such as reduced glutathione and ascorbate-2-phosphate salt; insulin or an insulin replacement such as a zinc-containing compound including zinc chloride, zinc nitrate, zinc bromide and zinc sulfate; a collagen precursor such L-proline, L-hydroxyproline, and ascorbic acid; and a trace element such as $Ag^+$, $Al^{3+}$, $Ba^{2+}$, $Cd^{2+}$, $Co^{2+}$, $Cr^{3+}$, $Ge^{4+}$, $Se^{4+}$, $Br^-$, $I^-$, $Mn^{2+}$, $F^-$, $Si^{4+}$, $V^{5+}$, $Mo^{6+}$, $Ni^{2+}$, $Rb^+$, $Sn^{2+}$, and $Zr^{4+}$.

An example of the serum replacement is described in Japanese Patent Publication (Kohyo) No. 2001-508302 as "a supplement for serum-free culture medium of eukaryote", and the composition of a serum replacement can be determined as appropriate in view of the publication. Representative serum replacements are offered commercially as Serum Replacement for Embryonic Stem Cell (KSR) by Invitrogen, and readily available.

LIF, 2-ME, and KSR as described above may be usually adjusted to final concentrations of 1 to 10000 units/ml, 1 to 1000 μM, and 0.5 to 90% (v/v), respectively, and preferably to final concentrations of 100 to 1000 units/ml, 10 to 100 μM, and 5 to 20%, respectively, in a culture medium. The composition of the present invention and those ingredients may be added to a culture medium in a portion that provides the intended final concentrations, or two or more portions that totally provide the intended final concentrations. The pH of the culture media is usually adjusted to 7.0 to 8.2, preferably 7.3 to 7.9 with a bicarbonate.

The compositions and the culture media according to the present invention may be in a form of solution or a drying form. The solution may be a concentrated one (for example 1× to 1000×), which may be diluted as appropriate before the use. Liquids for diluting or dissolving the compositions or the culture media in a form of solution or a drying form include water, a buffered aqueous solution, and a physiological saline, and they may be readily selected as appropriate.

Preferably, the compositions and the culture media according to the present invention are sterilized to prevent any contamination. The sterilization methods include ultraviolet irradiation, heat sterilization, radiation, and filtration.

In order to proliferate pluripotent stem cells while retaining their pluripotency by the process for the culture according to the present invention, the culture media of the invention described above, preferably the media comprising a cell culture minimum medium supplemented with leukemia inhibitory factor, an antioxidant, a serum replacement and a composition of the present invention may be used to culture the pluripotent stem cells in a culture condition commonly used in the art.

Pluripotent stem cells include those derived from diverse animals such as mammals including a human, a monkey, a mouse, a rat, a hamster, a rabbit, a guinea pig, a bovine, a pig, a dog, a horse, a cat, a gout, and a sheep, birds, and reptilian, and the cells derived from the mammals are usually used. Examples of pluripotent stem cells include ES cells, EG cells, EC cells, APS cells, and MAP cells. Cells frequently used are ES cells from mice. The number of pluripotent stem cells to be cultured is not limited to a specific one, and the process for the culture according to the invention has an advantage that the process can produce a clonal cell population by proliferating and culturing one pluripotent stem cell.

Pluripotent stem cells to be cultured may be dependent on feeder cells, and are preferably independent from feeder cells. Feeder cell-dependent pluripotent stem cells may be changed to feeder cell-independent ones by repeatedly subculturing the former cells under the culture condition without any feeder cells, and selecting cells that meet the condition thus specified.

Specific procedures of the process for the culture of pluripotent stem cells according to the present invention can be conducted in accordance with the procedures and conditions commonly used in the art. For example, the procedures may be determined consulting the literatures such as Norio Nakatsuji ed., the Jikken Igaku supplementary volume, Posutogenomu Jidai no Jikken Kouza 4 "Kansaibou/kuron kenkyu purotokoru", YODOSHA (2001); Hogan, G. et al. ed.: Manipulation of mouse embryos: A Laboratory Manual, Cold Spring Harbor Laboratory Press, Plainview, N.Y. (1994); and Robertson, E. J., ed.: teratocarcinoma and embryonic stem cell, A Practical Approach, IRL Press Oxford, UK (1987).

Typical procedures for the subculture and typical culture conditions are described below. In order to subculture ES cells, grown ES cells are first rinsed with phosphate buffered saline (PBS) once to twice, and then a sufficient amount of a trypsin-EDTA solution (0.25% trypsin-1 mM EDTA in PBS) is added to and covered over the cells, followed by leaving the cells for five minutes. Subsequently, a PBS containing a trypsin inhibitor or an ES cell culture minimum medium containing a serum (CCMM+LIF+2-ME) is added thereto, and the cell mass is separated by pipetting. The cell suspension is usually centrifuged to sediment the cells. After removing the supernatant, the sedimented cells are resuspended in an ES cell culture minimum medium containing a serum or a serum replacement, and a portion of the suspension is seeded into a feeder cell layer, or a gelatinated plastic plate, followed by incubating the cells at 37° C. in 5% $CO_2$.

As an embodiment of the present process, the culture medium of the present invention that is warmed at 37° C. is added to a gelatinated plastic plate which is treated with a 0.1% (w/v) gelatin solution, and therein pluripotent stem cells are seeded at 10 to 1000 cells per 1 $cm^2$. The plate is placed into a $CO_2$ incubator, and incubated at 37° C. in 5% $CO_2$. Developed colony (for example, E14tg2a cells are grown within seven days) is again seeded in a fresh medium to conduct the subculture, and at this time a PBS containing a trypsin inhibitor is preferably used.

Preferred example of a condition that the cells are seeded "at a lower density than that which allows adjacent pluripotent stem cells to interact with each other so as to induce the proliferative, undifferentiated pluripotent stem cells" specifically includes a condition at 1 cell/$mm^2$ or less. A step to obtain a clonal population of pluripotent stem cells from one cell should meet this condition on the establishment of a homogenous cell line of pluripotent stem cells or the proliferation of pluripotent stem cells genetically manipulated.

The preferred embodiment of the present invention involves no use of feeder cells and serums, and therefore save the needs for screening of a serum lot, and selecting and incubating a feeder cell, which are usually conducted in the cell culture. Culture media comprising the known ingredients according to the present invention makes it possible to proliferate single feeder cell-independent pluripotent stem cells while maintaining the cells in an undifferentiated state on a gelatin-coated plate under a condition that the cells are seeded at a lower density.

Further, present invention provides a process for screening for an agent that is capable of proliferating pluripotent stem cells while maintaining the cells in an undifferentiated state, when added to a cell culture medium without feeder cells and serums. Specifically, the process comprises culturing feeder cell-independent pluripotent stem cells (for example, mouse ES cells) in a culture medium comprising a cell culture minimum medium supplemented with leukemia inhibitory factor, a serum replacement, an antioxidant, and a candidate agent, checking the presence or the absence of the produced colony of undifferentiated pluripotent stem cells, and selecting a candidate agent that shows a significant positive signal.

The formation of a colony of the undifferentiated cells may be checked morphologically using protein staining methods including Leischman staining. Undifferentiated cell markers such as alkaline phosphatase, and SSEA-1, 3, 4 antigen can be also used, and they are detected with an antibody. Additionally, the expressions of Oct-3/4 gene and Rex-1 gene occur characteristically in undifferentiated cells, and therefore they may be used as a means for the check. Usually, a combination of those methods is used to check for the undifferentiated cells.

A composition of a typical culture medium and a typical culture condition for conducting the screening process described above are as follows:

Composition of a typical culture medium:
    GMEM, 10% KSR, 10 µM 2-ME, and 1000 U/ml LIF;
    0.1 mM non-essential amino acid, and 1 mM sodium pyruvate;

The number of pluripotent stem cells to be seeded on the medium: One ml of the culture is used per one cm², and 100 cells are seeded.

Culture condition: 37° C., 5% $CO_2$;

Means for checking and observation: The medium is checked after seven days, and the number of colony of undifferentiated pluripotent stem cells (/1 cm²) is estimated according to the following table.

| Number of colony of undifferentiated cells (/cm²) | Estimation |
|---|---|
| 0 | – |
| 1 to 5 | +1 |
| 6 to 10 | +2 |
| 10 以上 | +3 |

The process for the culture according to the present invention makes it possible to produce a clonal population of pluripotent stem cells by culturing and proliferating one pluripotent stem cell. This provides an advantage when a population of pluripotent stem cells, of which the genome is altered, is necessary, and when a transgenic animal is produced.

As a medium for the culture of a representative example of pluripotent stem cell, ES cells, a culture medium comprising a cell culture minimum medium supplemented with leukemia inhibitory factor (1), a serum (2), 2-mercaptoethanol (3), and feeder cells (4) has been used. When (1) to (3) are comprised, then feeder cell-independent ES cells may be cultured on a gelatin-coated plate to which the cells are directly adhered, and (4) is not necessary. When (4) is comprised, (2) may be substituted with a serum replacement (5), which makes it possible to culture the ES cells without a serum. The present invention provides a process for the culture of ES cells in the absence of feeder cells (4), which comprises adding an inhibitor of an adenylate cyclase activity (6) to such medium as that without a serum.

The aforementioned descriptions illustrate an embodiment of the present invention in which "a condition that an adenylate cyclase activity is inhibited" involves the addition of an inhibitor of an adenylate cyclase activity to a medium or the combination of the inhibitor with the medium, but such a condition can be fulfilled by different suitable methods. For example, a method for inhibiting the expression of an adenylate cyclase gene in a pluripotent stem cells by means of mRNA or RNAi, for example, and a method for expressing a molecule that inhibits an adenylate cyclase activity via genetic engineering procedures by means of an antagonistic variant, can be utilized according to the invention.

In another aspect, the present invention provides a medium supplement for the culture of pluripotent stem cells, which comprises at least one inhibitor of an adenylate cyclase activity. Preferably, the inhibitor of an adenylate cyclase activity is selected from the group consisting of SQ22536 (9-(tetrahydro-2-furanyl)adenine), 2',5'-dideoxyadenosine, 9-cyclopentyladenine, 2',5'-dideoxyadenosine 3'-diphosphate, 2',5'-dideoxyadenosine 3'-monophosphate, and MDL-12,330A (cis-N-(2-phenylcyclopentyl)azacyclotridec-1-en-2-amine), or is selected from the group consisting of adrenocorticotropic hormone (ACTH), brain natriuretic peptide (BNP), pituitary adenylate cyclase activating polypeptide (PACAP), and a peptide having a physiological activity substantially similar to them.

In a further aspect, the invention provides a medium for the culture of pluripotent stem cells, which comprises any one of the medium supplements as described above. Preferably, the medium is free of a feeder cell, and/or a serum. More preferably, the medium is free of both feeder cell and serum. The medium may comprise a cell culture minimum medium as a minimal essential medium, and may comprise further a differentiation inhibitory factor, a serum replacement and an antioxidant.

In a still further aspect, the invention provides a process for the culture of pluripotent stem cells, which comprises culturing the pluripotent stem cells under a condition that an adenylate cyclase activity is inhibited, said process allowing to proliferate the pluripotent stem cells while maintaining the cells in an undifferentiated state. In the process, the condition that an adenylate cyclase activity is inhibited may involve the use of an inhibitor of an adenylate cyclase activity. Also, the culture process may be performed using the medium as described above. According to the culture process, one pluripotent stem cell can be cultured to provide a clonal population of the cells, and alternatively, pluripotent stem cells can be cultured in the medium as described above to provide a clonal population of the cells in which the pluripotent stem cells are not proliferated while maintaining an undifferentiated state under the condition that neither feeder cells and/or serums, nor the medium supplement as described above is used. According to the culture process, one pluripotent stem cell is preferably cultured in the medium as described above to provide a clonal population of the cells. In the process, the pluripotent stem cells may be ES cells, or may be derived from a mammal. The pluripotent stem cells may be also derived from a human.

In a further aspect, the invention also provides an undifferentiated pluripotent stem cell that retains its pluripotency, which is proliferated according to the process as described above.

In a still further aspect, the invention provides a process for the culture of pluripotent stem cells, which comprises culturing the pluripotent stem cells under a condition that an adenylate cyclase activity is inhibited, said process allowing to establish the undifferentiated pluripotent stem cells. In the process, the condition that an adenylate cyclase activity is inhibited may involve the use of an inhibitor of an adenylate cyclase activity. The culture process may be performed using the medium as described above. In the culture process, the pluripotent stem cells may be ES cells, or may be derived from a mammal. The pluripotent stem cells may be also derived from a human.

In a further aspect, the invention also provides an undifferentiated pluripotent stem cell that retains its pluripotency, which is established according to the process as described above.

The following working examples are presented for purpose of the demonstration of the invention that makes it possible to culture ES cells in a medium prepared from all of the known ingredients, without a serum and a feeder medium. Those examples are not intended to be limiting the invention in any respect.

EXAMPLE 1

One hundred of the feeder cell-independent ES cells (E14tg2a (Hooper, M. et al., Nature, 325, 292 (1987)), CGR8 (Mountford, P. et al., Proc. Natl. Acad. Sci. USA, 91, 4303 (1994)), and ES cells derived therefrom) were incubated on the gelatinated 12-well plate treated with a 0.1% (w/v) gelatin solution at 37° C. in 5% $CO_2$ in one ml of a culture medium of Glasgow minimum essential medium (GMEM; Sigma) used as a cell culture minimum medium supplemented with (1)

1×10³ U/ml LIF (ESGRO, Invitrogen), (3) 0.1 µM 2-mercaptoethanol (Nacalai Tesque), and (5) 10% (v/v) KSR (Invitrogen) per well.

Five days or more after the incubation, the supernatant was removed by aspiration, and then a Leischman staining liquid (1.5 g Leischman Staining: Sigma/L methanol) was added to the plate until the liquid covered all of the surface of the plate. The plate was left at room temperature for 10 minutes, and rinsed with water (Leischman staining). For the blue-stained colonies, no formation of colonies that maintained their morphology in an undifferentiated state was shown by the naked eye and light microscopy (FIG. 1 (g)). When the ES cells were incubated in a culture medium wherein the medium described above was supplemented with 0.3% (v/v) FCS (2), an average of 17 colonies of undifferentiated cells was observed (FIG. 1 (d)). This showed that the composition of (1)+(3)+(5) should lack an ingredient essential for the formation of undifferentiated cell colonies, which was comprised in FCS (2). Further, a formation of colonies of undifferentiated cells was observed when the ES cells were incubated at 1000 or more per well in the culture medium having the same composition ((1)+(3)+(5)). When the conditioned medium (CM) was added to a culture medium at a final concentration of 10% (v/v), and 100 ES cells per well were incubated therein, then an average of 7 colonies of undifferentiated cells was observed (FIG. 1 (f)). This showed that the ES cells themselves secreted an ingredient essential for the formation of undifferentiated cell colonies.

Subsequently, a candidate peptide that had been selected from diverse known growth factors, cytokines, peptide hormones and the like, was added to the culture medium comprising (1)+(3)+(5), and the ES cells were incubated therein at 37° C. in 5% $CO_2$ so that a capability of the candidate to form a colony of undifferentiated cells was determined. As a result, a formation of colonies of undifferentiated ES cells having the apparent morphology was observed on the medium supplemented with 1 µM adrenocorticotropic hormone, 1 µM brain natriuretic peptide, and 1 µM pituitary adenylate cyclase activating polypeptide (FIG. 1 (e): ACTH was used as a peptide). It should be noted that FIG. 1 (a) to (c) show the results obtained from the medium consisting of GMEM, LIF and 2-ME, supplemented with FCS+feeder cells, KSR+feeder cells, and FCS, respectively.

The ES cells which were composed in the colonies formed by the supplement with those peptide hormones were checked that they were positive in the staining test for alkaline phosphatase activity, which is a marker of the undifferentiated state (FIG. 1), and that a transcription factor Oct-3/4 was expressed by the activity of a reporter gene transducted via homologous gene recombination. This shows that those peptides should have a capability to form a colony of undifferentiated cells, similarly to FCS and CM.

EXAMPLE 2

ACTH, which had been shown to have the capability at the lowest concentration among the candidate peptides tested in Example 1, and fragments thereof, were used to examine their significance. In a similar manner to the above, ACTH and the fragments thereof were added to the culture medium at a final concentration of 1 µM wherein (1) LIF, (3) 2-ME, and (5) KSR were supplemented to a cell culture minimum medium. As a result, ACTH (1-39), ACTH (1-24), and ACTH (11-24) showed to have the capability, whereas ACTH (18-39) showed to have no capability. ACTH (1-24) showed to have the most potent capability among the fragments having a capability, and showed the formation of the colony of undifferentiated cells even at a final concentration of 0.1 µM. Formation rate of undifferentiated cell colonies, and cell proliferation rate in the case of the supplementation of 10 µM ACTH (1-24) were equivalent to that in the case of 0.3% FCS or 10% CM.

The results described above show that a culture medium wherein a cell culture minimum medium as used as a minimal essential medium was supplemented with a peptide hormone such as (1) LIF, (3) 2-ME, (5) KSR+(6) ACTH, makes it possible to proliferate ES cells while maintaining the cells in an undifferentiated state, which retain their pluripotency, even without serums or feeder cells.

EXAMPLE 3

In order to examine what kind of signal transduction ACTH involves within cells to proliferate ES cells while maintaining the cells in an undifferentiated state, which retain their pluripotency, even without serums or feeder cells, various inhibitors of the signal transduction were added to the culture medium to observe the proliferations of ES cells.

ACHT has been known to activate an ACTH receptor belonging to G-protein-coupled receptor families, which receptor activates an adenylate cyclase activity through the activation of trimeric G proteins containing the $G_{\alpha\,s}$ subunit. Now, to a cell culture minimum medium supplemented with (1) 1×10³ U/ml LIF, (3) 0.1 µM 2-ME, (5) 10% (v/v) KSR, and (6) 10 µM ACTH, an inhibitor of an adenylate cyclase activity, SQ22536 (9-(tetrahydro-2-furanyl)adenine) (Sigma) at 100 µM, was further added, and the resultant medium was used to culture the ES cells in a similar manner to that of Example 1. As a result, no formation of colonies of undifferentiated cells was unexpectedly inhibited on the 7th day, and the size of individual colonies was significantly increased.

In order to check the effect of sole SQ22536, a cell culture minimum medium supplemented with (1) 1×10³ U/ml LIF, (3) 0.1 µM 2-ME, (5) 10% (v/v) KSR, and (7) SQ22536 100 µM was used to culture the ES cells in a similar manner to that of Example 1. As a result, an average of nine colonies of undifferentiated cells was observed. Further, even when the medium added with another inhibitor of an adenylate cyclase activity, 2',5'-dideoxyadenosine (Sigma) 500 µM, was used, an average of eight colonies of undifferentiated cells was observed. Those results show that the inhibition of an adenylate cyclase activity caused the formation of colonies of undifferentiated cells.

An adenylate cyclase activity via a G-protein-coupled receptor is usually inhibited through the activation of trimeric G proteins containing the $G_{\alpha\,i}$ subunit. In order to check whether or not the effect of ACTH mediates this signal transduction, an inhibitor of the $G_{\alpha\,i}$, pertussis toxin, was added to a cell culture minimum medium supplemented with (1) 1×10³ U/ml LIF, (3) 0.1 µM 2-ME, (5) 10% (v/v) KSR, and (6) 10 µM ACTH at a final concentration of 100 ng/ml, and the resultant medium was used to culture the ES cells in a similar manner to that of Example 1. As a result, the effect of ACTH was inhibited, and the size of the colonies of undifferentiated cells was drastically decreased. This shows that the effect of ACTH on the formation of colonies of undifferentiated cells mediates the activation of the $G_{\alpha\,i}$. Further, this also shows that ACTH would bind to a G-protein-coupled receptor that is different from a receptor specific to ACTH in ES cells since the ACTH receptor is associated with the $G_{\alpha\,s}$.

Those results as shown above demonstrated that the effect of ACTH on the formation of colonies of undifferentiated cells should mediate the following signal transductions: 1)

ACTH binds to a G-protein-coupled receptor that is associated with the $G_{\alpha i}$, 2) then the $G_{\alpha i}$ is activated, and then 3) an adenylate cyclase activity is inhibited. Accordingly, this suggests that any method could be selected so long as the method inhibits an adenylate cyclase activity, in order to proliferate ES cells while maintaining the cells in an undifferentiated state in a medium without serums or feeder cells.

EXAMPLE 4

The undifferentiated ES cells derived from the colonies obtained by the culture with 1 nM adrenocorticotropic hormone in Example 1 as described above were further subcultured twice, and the resultant cells were injected into the mouse blastocyst to complete the transplantation into the pseudopregnant mouse uterus. As a result, 33 litters were produced from 100 transplanted embryos, and as many as 30 litters survived three weeks or more after birth, of which the 17 litters were the chimeric mice that had an ES cell contribution ratio of 70% or more in view of their hair color. Among the 17 litters, 14 litters are female, which showed so-called "male distortion", and the inbreeding showed the contribution of the ES cells to the germ cell line. This demonstrated that the culture conditions described herein should be sufficient to retain the pluripotency of ES cells.

EXAMPLE 5

Thirty embryos at blastocyst stage of 3.5 days old were removed from C57BL/6 inbred mouse strains, and the inner cell masses isolated from the embryos by immunosurgery were individually incubated in the culture medium consisting of CCMM, (1) $1 \times 10^3$ U/ml LIF, (3) 0.1 µM 2-ME, 0.1 mM non-essential amino acids, 1 mM sodium pyruvate, (5) 10% (v/v) KSR, and (6) 10 µM ACTH on a plate coated with fibronectin. This resulted in the initiation of the proliferations of at least two inner cells, which finally established ES cell lines. This demonstrated that the present culture process should be useful in not only the culture of the established ES cells, but also in the establishment of fresh ES cell lines.

The invention claimed is:

1. A process for culturing mouse pluripotent stem cells, which comprises culturing the mouse pluripotent stem cells in a medium comprising leukemia inhibitory factor (LIF), an antioxidant and an inhibitor of adenylate cyclase activity, said process allowing the mouse pluripotent stem cells to proliferate or establish while maintaining the cells in an undifferentiated state.

2. The process according to claim 1, wherein the culture process is performed using a minimal culture medium.

3. The process according to claim 1, wherein the pluripotent stem cells are ES cells.

4. A process for the preparation of a clonal population of undifferentiated mouse pluripotent stem cells, which comprises culturing the undifferentiated mouse pluripotent stem cells in a medium comprising leukemia inhibitory factor (LIF), an antioxidant and an inhibitor of adenylate cyclase activity.

5. A process for the preparation of a clonal population of undifferentiated mouse pluripotent stem cells, which comprises isolating undifferentiated pluripotent stem cells from a living body of a mouse, and culturing the undifferentiated mouse pluripotent stem cells in a medium comprising leukemia inhibitory factor (LIF), an antioxidant and an inhibitor of adenylate cyclase activity.

6. The process according to claim 4, wherein the culture process is performed using a minimal culture medium.

7. The process according to claim 4, wherein one pluripotent stem cell is cultured to provide a clonal population of the cells.

8. The process according to claim 4, wherein pluripotent stem cells are cultured in a medium free of feeder cells or free of serum or free of both, to provide a clonal population of the cells, in which the pluripotent stem cells are seeded at a lower density than that which allows adjacent pluripotent stem cells to interact with each other, so as to induce the proliferation of undifferentiated pluripotent stem cells.

9. The process according to claim 4, wherein one pluripotent stem cell is cultured in a medium free of feeder cells or free of serum or free of both, to provide a clonal population of the cells.

10. The process according to claim 4, wherein the pluripotent stem cells are ES cells.

11. The process of claim 1, wherein the inhibitor of adenylate cyclase activity is selected from the group consisting of SQ22536 (9-(tetrahydro-2-furanyl)adenine), 2',5'-dideoxyadenosine, 9-cyclopentyladenine, 2',5'-dideoxyadenosine 3'-diphosphate, 2',5'-dideoxyadenosine 3'-monophosphate, and MDL-12,330A (cis-N-(2-phenylcyclopentyl)azacyclotridec-1-en-2-amine).

12. The process according to claim 1, wherein the medium is free of feeder cells or of serum or free of both.

13. The process according to claim 1, wherein the medium further comprises a second differentiation inhibitory factor and a serum replacement.

14. The process according to claim 4, wherein the medium further comprises a second differentiation inhibitory factor and a serum replacement.

15. The process of claim 1, wherein the antioxidant is 2-mercaptoethanol, the inhibitor of adenylate cyclase activity is SQ22536, and further comprising a serum replacement, KSR.

* * * * *